(12) United States Patent
Tohma et al.

(10) Patent No.: US 6,172,268 B1
(45) Date of Patent: Jan. 9, 2001

(54) METHOD FOR PRODUCING AN OPTICALLY ACTIVE 1-SUBSTITUTED 2-PROPANOL

(75) Inventors: Toshihiko Tohma; Tomoyuki Asai, both of Kanagawa (JP)

(73) Assignee: Asahi Glass Company, Limited, Tokyo (JP)

( * ) Notice: Under 35 U.S.C. 154(b), the term of this patent shall be extended for 0 days.

(21) Appl. No.: 09/493,019

(22) Filed: Jan. 28, 2000

(51) Int. Cl.$^7$ .............................. C07C 41/01; C07C 43/23
(52) U.S. Cl. .......................... 568/588; 568/648; 568/649; 568/656
(58) Field of Search ..................................... 568/648, 649, 568/656, 588

(56) References Cited

PUBLICATIONS

Database CAPLUS on STN, Acc. No. 1999:147769. Matsui et al., 'Method for preparation of glycol ethers by reaction of epoxides or alpha–halo alcohols with alcohols.' JP 11060529 (abstract), 1999.*

\* cited by examiner

*Primary Examiner*—Samuel Barts
*Assistant Examiner*—Brian J. Davis
(74) *Attorney, Agent, or Firm*—Oblon, Spivak, McClelland, Maier & Neustadt, P.C.

(57) ABSTRACT

A method for producing an optically active 1-substituted 2-propanol of the following formula 1, which comprises reacting a hydroxy aromatic compound of the following formula 2 with an optically active propylene oxide in the presence of a catalyst:

AOH           Formula 2

$CH_3C^*H(OH)CH_2OA$           Formula 1 wherein A is a univalent aromatic group, and C\* is an asymmetric carbon atom.

10 Claims, No Drawings

METHOD FOR PRODUCING AN OPTICALLY ACTIVE 1-SUBSTITUTED 2-PROPANOL

BACKGROUND OF THE INVENTION

1. Field of the Invention

The present invention relates to a method for producing an optically active 1-substituted 2-propanol which is useful as a starting material for pharmaceuticals or agricultural chemicals, particularly as an intermediate for synthetic antibacterial agents.

2. Discussion of Background

The following methods have been proposed for the synthesis of optically active 1-aryloxy-2-propanols among optically active 1-substituted 2-propanols.

(1) A method of reacting optically active 2-O-tetrahydropyranylpropane-1,2-diol with a fluorobenzene derivative (EP322815A).

(2) A method of reacting optically active 2-O-tetrahydropyranylpropane-1,2-diol with a phenol derivative by means of a Mitsunobu reagent (JP-A-1-250369).

(3) A method of reducing a 1-aryloxy-2-propanone by means of a microorganism (JP-A-3-183469, JP-A-5-68577).

(4) A method of converting a racemic modification of a 1-aryloxy-2-propanol to an optically active 1-aryloxy-2-acyloxypropane by means of a microorganism, followed by hydrolysis (JP-A-4-267890).

However, the above methods have the following problems.

The methods (1) and (2) require many steps for the synthesis of the optically active starting material. The methods (3) and (4) utilize microorganisms and thus have drawbacks specific to microbial reactions. For example, they have problems such that the volume efficiency is poor, and an antipode having an absolute configuration opposite to the desired optically active substance, will be obtained. Namely, the conventional methods have had problems in their industrial application.

SUMMARY OF THE INVENTION

The present invention has been made to solve the above problems, and it is an object of the present invention to provide a method for producing an optically active 1-substituted 2-propanol which is useful as an intermediate for e.g. synthetic antibacterial agents. That is, the present invention provides a method for producing an optically active 1-substituted 2-propanol of the following formula 1, which comprises reacting a hydroxy aromatic compound of the following formula 2 with, an optically active propylene oxide in the presence of a catalyst:

 AOH                                      Formula 2

 CH$_3$C*H(OH)CH$_2$OA                    Formula 1 wherein A is a univalent aromatic group, and C* is an asymmetric carbon atom.

DETAILED DESCRIPTION OF THE PREFERRED EMBODIMENTS

Now, the present invention will be described in detail.

In the hydroxy aromatic compound (formula 2) in the present invention, A is a univalent aromatic group having one hydrogen atom on an aromatic ring removed from a compound having the aromatic ring. The compound having the aromatic ring may, for example, be an aromatic hydrocarbon compound such as benzene, naphthalene, anthracene, biphenyl or indene, a compound having an aromatic hetero ring such as pyridine, furan, thiophene, pyridazine, pyrimidine, pyrazine, 1,3,5-triazine, isoquinoline, quinoxaline or naphthylizine, or an aromatic hydrocarbon compound or a compound having a hetero ring, which has a substituent.

In the present invention, A is preferably an aryl group which is a residue having one hydrogen atom removed from an aromatic hydrocarbon compound, or a substituted aryl group. Namely, as the hydroxy aromatic compound (formula 2) in the present invention, a hydroxyaryl compound of the following formula 2a, is preferred:

 A$^r$OH                                  Formula 2a wherein A$^r$ is an aryl group or a substituted aryl group.

When A$^r$ is a substituted aryl group, such a substituted aryl group is a group having at least one hydrogen atom in the aryl group substituted by a substituent. As such a substituent, a halogen atom, a nitro group, a cyano group, a carbamoyl group, a monoacylamino group or a diacylamino group is, for example, preferred. As the halogen atom, a chlorine atom, a bromine atom or a fluorine atom is preferred. As the monoacylamino group, an acetylamino group is preferred, and as the diacylamino group, a diacetylamino group is preferred.

As the substituted aryl group, a substituted phenyl group is preferred. The number of substituents in the substituted phenyl group is preferably from 1 to 4, particularly preferably from 1 to 3. Further, when the number of substituents in the substituted phenyl group is two or more, such substituents may be the same or different.

The following compounds may be mentioned as specific examples of the hydroxy aromatic compound (formula 2) in the present invention. However, there is no particular limitation as to the positions at which the hydroxyl groups and the substituents are bonded in the following hydroxy aromatic compounds.

Examples of the hydroxy aromatic compound (formula 2) other than the hydroxyaryl compound (formula 2a):

Hydroxypyridine, fluorohydroxypyridine, chlorohydroxypyridine, trifluoromethylhydroxypyridine, hydroxyfuran, fluorohydroxyfuran, chlorohydroxypyrimidine, hydroxypyrazine, chlorohydroxyisoquinoline, and hydroxynaphthylidine.

Examples of the hydroxyaryl compound (formula 2):

Phenol, nitrophenol, cyanophenol, chlorophenol, fluorophenol, chloronitrophenol, fluoronitrophenol, chlorofluoronitrophenol, and difluoronitrophenol.

In the present invention, the hydroxy aromatic compound (formula 2) is preferably a hydroxyaryl compound (formula 2a), particularly preferably a compound of the formula (formula 2a) wherein Ar is a substituted phenyl group. Further, the hydroxyaryl compound (formula 2a) is preferably one wherein Ar is a phenyl group substituted by a nitro group and a halogen atom. As such a halogen atom, a fluorine atom and/or a chlorine atom is preferred.

Further, the hydroxyaryl compound (formula 2a) is preferably a nitrophenol of the following formula 2b:

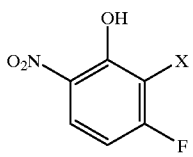

Formula 2b wherein X is a fluorine atom or a chlorine atom.

Further, the following compounds may be mentioned as specific examples other than nitrophenols (formula 2b) among hydroxy aromatic compounds (formula 2) of the present invention.

6-Chloro-2-nitrophenol,
5-chloro-2-nitrophenol,
4-chloro-2-nitrophenol,
3-chloro-2-nitrophenol,
6-fluoro-2-nitrophenol,
5-fluoro-2-nitrophenol,
4-fluoro-2-nitrophenol,
3-fluoro-2-nitrophenol.

The following compounds may be mentioned as specific examples of the nitrophenols (formula 2b).

2-Chloro-3-fluoro-6-nitrophenol,
2,3-difluoro-6-nitrophenol.

In the present invention, the hydroxy aromatic compound (formula 2) is reacted with an optically active propylene oxide.

The optically active propylene oxide is a propylene oxide which contains either a propylene oxide wherein the absolute configuration of asymmetric carbon atom is R (i.e. R-propylene oxide) or a propylene oxide wherein such an absolute configuration is S (i.e. S-propylene oxide) excessively. The optical active propylene oxide may be one containing either R-propylene oxide or S-propylene oxide excessively.

The reaction of the present invention proceeds while the absolute configuration of the asymmetric carbon atom of the propylene oxide is maintained. Accordingly, a propylene oxide may be employed which has an absolute configuration corresponding to the absolute configuration of the desired compound. The optically active propylene oxide can be obtained by e.g. kinetic resolution as disclosed in a literature (Science, 277, 936 (1997)). The optically active propylene oxide is preferably one having an optical purity of from 0.1 to 100% ee (enantio excess), more preferably from 10 to 100% ee, most preferably from 30 to 100% ee.

The optically active propylene oxide is used preferably in an amount of from 10 to 500 mol %, more preferably from 50 to 300 mol %, to the hydroxy aromatic compound (formula 2).

The reaction of the present invention is carried out in the presence of a catalyst. As the catalyst, alumina, a base or a metal complex compound is, for example, preferred. The alumina may, for example, be W-200 (tradename, manufactured by Woelm Co.), and the base may be an organic base or an inorganic base. The organic base is preferably triethylamine or diisopropylethylamine, and the inorganic base is preferably sodium hydroxide, sodium carbonate, sodium hydrogencarbonate, potassium hydroxide, potassium carbonate or potassium hydrogencarbonate.

The catalyst in the present invention is preferably a metal complex compound consisting of a combination of a center metal and a ligand. As the center metal of the metal complex compound, cobalt, manganese, chromium or nickel may, for example, be mentioned, and as the ligand, N,N'-bis(salicylidene)ethylenediamine (salen), N,N'-bis(salicylidene)-1,2-benzenediamine (salphen) or a porphyrin may, for example, be mentioned.

Further, the metal complex compound is preferably cobaloxime, cobalt$^{II}$ tetraphenylporphyrin (Co$^{II}$TPP), or a metal complex compound of the following formula 3, particularly preferably a metal complex compound of the following formula 3.

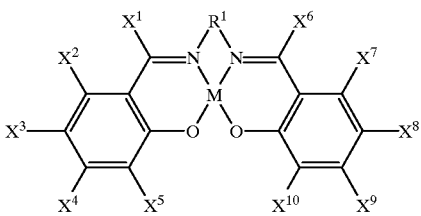

Formula 3 wherein $R^1$ is a $C_{1-20}$ alkylene group, a substituted $C_{1-20}$ alkylene group, a $C_{3-20}$ cycloalkylene group, an arylene group or a substituted arylene group, each of $X^1$ to $X^{10}$ which are independent of one another, is a hydrogen atom, a halogen atom, an alkyl group, a cycloalkyl group, an alkenyl group, an alkynyl group, a hydroxyl group, an amino group, a nitro group, a carbamoyl group, a carboxyl group or a silyl group which may be substituted, and M is $M^1$ wherein $M^1$ is a bivalent metal atom or a bivalent metal ion, $M^2$—$A^2$ wherein $M^2$ is a bivalent metal atom or a trivalent metal atom, and $A^2$ is a ligand, or $M^3$—$A^3$ wherein $M^3$ is a trivalent metal atom, and $A^3$ is a counter ion.

When $R^1$ in the metal complex compound (formula 3) is a $C_{1-20}$ alkylene group, such a group is preferably a methylene group, an ethylene group, a trimethylene group, a propylene group, a tetramethylene group or a pentamethylene group.

When the $R^1$ is a substituted $C_{1-20}$ alkylene group, such a group is a group having at least one hydrogen atom of a $C_{1-20}$ alkylene group substituted. The substituted $C_{1-20}$ alkylene group is preferably an alkylene group substituted by an alkyl group or an alkylene group substituted by an aryl group, more preferably an alkylene group substituted by an aryl group, most preferably a 1,2-diphenylethylene group. When $R^1$ is a $C_{3-20}$ cycloalkylene group, such a group is preferably a cyclohexylene group, particularly preferably a 1,2-cyclohexylene group. When $R^1$ is an arylene group, such a group is preferably a phenylene group, particularly preferably a 1,2-phenylene group or a 1,3-phenylene group.

When $R^1$ is a substituted arylene group, such a group is preferably an alkyl group-substituted arylene group, particularly preferably a 3,6-di-t-butyl-1,2-phenylene group.

In the metal complex compound (formula 3), each of $X^1$ to $X^{10}$ which are independent of one another, is a hydrogen atom, a halogen atom, an alkyl group, a cycloalkyl group, an alkenyl group, an alkynyl group, a hydroxyl group, an amino group, a nitro group, a carbamoyl group, a carboxyl group or a silyl group which may be substituted.

When any one of $X^1$ to $X^{10}$ is a halogen atom, such a halogen atom is preferably a fluorine atom, a chlorine atom or a bromine atom, particularly preferably a fluorine atom or a chlorine atom. When any one of $X^1$ to $X^{10}$ is an alkyl group, such an alkyl group is preferably a $C_{1-20}$ alkyl group, particularly preferably a methyl group, an ethyl group, a butyl group or a t-butyl group. When any one of $X^1$ to $X^{10}$ is a cycloalkyl group, such a cycloalkyl group is preferably a $C_{3-20}$ cycloalkyl group, particularly preferably a cyclopentyl group or a cyclohexyl group. When any one of $X^1$ to $X^{10}$ is an alkenyl group, such an alkenyl group is preferably a $C_{2-20}$ alkenyl group, particularly preferably a vinyl group. When any one of $X^1$ to $X^{10}$ is an alkynyl group, such an alkynyl group is preferably a $C_{2-20}$ alkynyl group, particularly preferably an ethynyl group.

In the metal complex compound (formula 3), M is $M^1$ wherein $M^1$ is a bivalent metal atom or a bivalent metal ion, $M^2$—$A^2$ wherein $M^2$ is a bivalent metal atom or a trivalent metal atom, and $A^2$ is a ligand, or $M^3$—$A^3$ wherein $M^3$ is a trivalent metal ion, and $A^3$ is a counter ion.

$M^1$ (a bivalent metal atom or a bivalent metal ion) is preferably $Co^{II}$, $Mn^{II}$ or $Ni^{II}$, or an ion thereof, particularly preferably $Co^{II}$.

$M^2$ (a bivalent metal atom or a trivalent metal atom) in $M^2$—$A^2$ may, for example, be $Co^{II}$, $Mn^{II}$, $Ni^{II}$, $Co^{III}$, $Mn^{III}$, $Ni^{III}$ or $Al^{III}$, preferably $Co^{II}$ or $Co^{III}$. $A^1$ (a ligand) is preferably an ether compound or an alcohol compound, particularly preferably tetrahydrofuran or ethanol.

$M^3$ (a trivalent metal ion) in $A^3$—$A^3$ may, for example, be an ion of $Co^{III}$, $Mn^{III}$, $Ni^{III}$ or $Al^{III}$, preferably an ion of $Co^{III}$. $A^3$ (a counter ion) is preferably a halogen anion, a carboxylic acid anion, or AO- wherein A is as defined above, particularly preferably AO- corresponding to the hydroxy aromatic compound (formula 2) used for the reaction.

The metal complex compound (formula 3) is preferably one wherein M is $M^1$, and particularly preferably, $M^1$ is $Co^{II}$ or $Co^{III}$.

The metal complex compound (formula 3) is preferably N,N'-bis(salicylidene)ethylenediaminocobalt$^{II}$ [$Co^{II}$(salen)] or N,N'-bis(salicylidene)-1,2-benzenediaminocobalt$^{II}$ [$Co^{II}$(salphen)].

As the metal complex compound (formula 3), an optically active one may be employed. Such an optically active metal complex compound (formula 3) tends to let either R-propylene oxide or S-propylene oxide react preferentially. Accordingly, when an optically active propylene oxide has a low optical purity, it is preferred to selectively use an optically active metal complex compound which can be a catalyst for the reaction of the propylene oxide to be reacted.

The optically active metal complex compound may be a compound of the formula 3 wherein an asymmetric center, an asymmetric axis or an asymmetric carbon atom is present. Particularly preferred is a compound wherein $R^1$ is a 1,2-cyclohexylene group. Such a compound has an asymmetric axis and thus will be optically active. The optically active metal complex compound is preferably (1R,2R)-N,N'-bis(3,5-di-t-butylsalicylidene)-1,2-cyclohexanediaminocobalt$^{II}$, or (1S,2S)-N,N'-bis(3,5-di-t-butylsalicylidene)-1,2-cyclohexanediaminocobalt$^{II}$.

The above-described metal complex compound (formula 3) is a compound disclosed in a literature (Tetrahedron Lett., 38, 773 (1997)), and it can readily be available as a commercial product.

The amount of the metal complex compound is preferably from $10^{-5}$ to 100 mol %, particularly preferably from 0.001 to 10 mol %, to the hydroxy aromatic compound (formula 2).

In a case where the reaction of the present invention is carried out in the presence of the metal complex compound (formula 3), it is preferred that a base is present. By the presence of the base, the reaction rate is accelerated. As the base, an organic base is preferred. Particularly preferred is triethylamine or diisopropylethylamine. The amount of the organic base is preferably from 0 to 200 mol %, particularly preferably from 80 to 130 mol %, to the hydroxy aromatic compound (formula 2).

The reaction of the present invention can be carried out in the presence or in the absence of a solvent for the reaction. When a solvent for the reaction is employed, it is preferred to select it from solvents which will not be involved in the reaction, and an organic solvent is preferred.

The organic solvent may, for example, be a hydrocarbon type solvent such as hexane, benzene, toluene, xylene, chlorobenzene or cyclohexane, a chlorine type solvent such as dichloromethane, chloroform or dichloroethane, an ether type solvent such as diethyl ether, tetrahydrofuran, ethylene glycol dimethyl ether, ethylene glycol diethyl ether, diisopropyl ether or methyl t-butyl ether, dichloromethane, methyl t-butyl ether, hexane, toluene or xylene. The amount of the solvent for reaction is preferably from 0 to 200 ml, particularly preferably from 0 to 1,200 ml, per mol of the hydroxy aromatic compound (formula 2).

The temperature for the reaction of the present invention is preferably from −20° C. to +100° C., particularly preferably from 0° C. to 30° C. The reaction time is preferably from 0.5 to 100 hours, particularly preferably from 0.5 to 40 hours.

By the reaction of the present invention, an optically active 1-substituted 2-propanol (formula 1) is obtainable. The optically active 1-substituted 2-propanol is preferably a compound of the following formula 1a, particularly preferably a compound of the following formula 1b. In the following formulae, the symbols are as defined above.

CH$_3$C*H(OH)CH$_2$OA'  Formula 1a

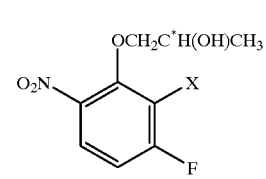

Formula 1b

The following compounds may be mentioned as specific examples other than the compound of the formula 1b among specific examples of the optically active 1-substituted 2-propanol (formula 1).

(2R or 2S)-1-(6-chloro-2-nitrophenoxy)-2-propanol,
(2R or 2S)-1-(5-chloro-2-nitrophenoxy)-2-propanol,
(2R or 2S)-1-(4-chloro-2-nitrophenoxy)-2-propanol,
(2R or 2S)-1-(3-chloro-2-nitrophenoxy)-2-propanol,
(2R or 2S)-1-(6-fluoro-2-nitrophenoxy)-2-propanol,
(2R or 2S)-1-(5-fluoro-2-nitrophenoxy)-2-propanol,
(2R or 2S)-1-(4-fluoro-2-nitrophenoxy)-2-propanol,
(2R or 2S)-1-(3-fluoro-2-nitrophenoxy)-2-propanol.

The following compounds may be mentioned as specific examples of the compound of the formula 1b.

(2R or 2S)-1-(2-chloro-3-fluoro-6-nitrophenoxy)-2-propanol,
(2R or 2S)-1-(2,3-difluoro-6-nitrophenoxy)-2-propanol.

The reaction product containing an optically active 1-substituted 2-propanol (formula 1) formed by the reaction, is usually preferably subjected to post treatment to obtain a product of high purity. The post treatment may be carried out by a method wherein the reaction product after completion of the reaction is extracted with an organic solvent, and the organic solvent extract is concentrated to isolate the optically active 1-substituted 2-propanol.

The optically active 1-substituted 2-propanol (formula 1) as the desired compound of the present invention, is a compound useful as a starting material or an intermediate for other compounds. In particular, a quinolone type antibacterial agent can be produced by using the compound as an intermediate.

Now, the present invention will be described in further detail with reference to an Example. However, it should be understood that the present invention is by no means restricted to such specific Example.

EXAMPLE

Preparation of (2R)-1-(2,3-difluoro-6-nitrophenoxy)-2-propanol

Into a 200 ml glass reactor, 600 mg (2.1 mmol) of N,N'-bis(salicylidene)ethylenediaminocobalt$^{II}$ (a metal complex compound of the formula 3, wherein $R^1$ is an ethylene group, and each of $X^1$ to $X^{10}$ is a hydrogen atom), 10.5 g (60 mmol) of 2,3-difluoro-6-nitrophenol, and 80 ml of methyl t-butyl ether were charged and stirred at room temperature for 2 hours in an air atmosphere. The solvent i.e. methyl t-butyl ether was distilled off under reduced pressure, and the reactor containing a dried brown solid was deaerated and filled with nitrogen. To this reactor, 8.4 g (65 mmol) of diisopropylethylamine, 5.8 g (100 mmol) of (R)-propylene oxide having an optical purity of 99.2% ee and 50 ml of toluene were added at room temperature and stirred at 40° C. for 15 hours in a nitrogen atmosphere. At that time, the conversion of 2,3-difluoro-6-nitrophenol was 86%.

50 ml of water and 50 ml of methyl t-butyl ether were added thereto, and the mixture was stirred and then left to stand still for liquid separation. The organic phase as the upper layer was washed sequentially with 30 ml of a saturated sodium hydrogencarbonate aqueous solution, 30 ml of 1N hydrochloric acid and 30 ml of water, dried by an addition of 5 g of magnesium sulfate, subjected to filtration and then concentrated, and the solvent was distilled off. As a remaining oily substance, 8.5 g (36 mmol) of (2R)-1-(2,3-difluoro-6-nitrophenoxy)-2-propanol, was obtained. The yield was 61%, based on 2,3-difluoro-6-nitrophenol, and the value of $[\alpha]_D^{20}$ was +3.3° (c=1, methanol). (The specific rotatory power $[\alpha]_D^{20}$ value disclosed in JP-A-2-178287 is +3.3° (c=1, methanol).)

According to the method of the present invention, an optically active 1-substituted 2-propanol compound can be produced in a higher yield and in a simpler manner than the conventional methods.

What is claimed is:

1. A method for producing an optically active 1-substituted 2-propanol of the following formula 1, which comprises reacting a hydroxy aromatic compound of the following formula 2 with an optically active propylene oxide in the presence of a catalyst:

AOH      Formula 2

CH$_3$C*H(OH)CH$_2$OA      Formula 1 wherein A is a univalent aromatic group, and C* is an asymmetric carbon atom, wherein said catalyst is a metal complex catalyst of the following formula 3:

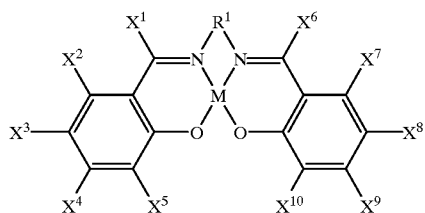

Formula 3 wherein $R^1$ is alkylene group, a substituted $C_{1-20}$ alkylene group, a $C_{3-20}$ cyloalkylene group, an arylene group or a substituted arylene group, each of $X^1$ to $X^{10}$ which are independent of one another, is a hydrogen atom, a halogen atom, an alkyl group, a cycloalkyl group, an alkenyl group, an alkynyl group, a hydroxyl group, an amino group, a nitro group, a carbamoyl group, a carboxyl group or a silyl group which may be substituted, and M is $M^1$ wherein $M^1$ is a bivalent metal atom or a bivalent metal ion, $M^2$—$A^2$ wherein $M^2$ is a bivalent metal atom or a trivalent metal atom, and $A^2$ is a ligand, or $M^3$—$A^3$ wherein $M^3$ is a trivalent metal atom, and $A^3$ is a counter ion.

2. The method according to claim 1, wherein A is an aryl group or a substituted aryl group.

3. The method according to claim 1, wherein A is an aryl group or an aryl group having at least one of the hydrogen atoms in the aryl group substituted by a halogen atom, a nitro group, a cyano group, a carbamoyl group, a monoacylamino group or a diacylamino group.

4. The method according to claim 1, wherein the hydroxy compound of the formula 2 is a nitrophenol of the following formula 2b:

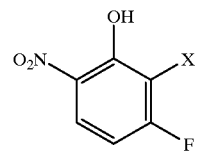

Formula 2b wherein X is a fluorine atom or a chlorine atom.

5. The method according to claim 4, wherein X is a fluorine atom.

6. The method according to claim 1, wherein M is a bivalent cobalt atom.

7. The method according to claim 1, wherein each of $X^1$ to $X^{10}$ is a hydrogen atom.

8. The method according to claim 1, wherein the reaction is carried out in the presence of a base.

9. The method according to claim 4, wherein the reaction is carried out in the presence of a base.

10. The method according to claim 5, wherein the reaction is carried out in the presence of a base.

* * * * *